United States Patent
Ishii et al.

(10) Patent No.: US 10,343,146 B2
(45) Date of Patent: *Jul. 9, 2019

(54) COMPOSITE OXIDE CATALYST, METHOD FOR PRODUCING THE SAME, AND METHOD FOR PRODUCING UNSATURATED NITRILE

(71) Applicant: ASAHI KASEI CHEMICALS CORPORATION, Tokyo (JP)

(72) Inventors: Yusuke Ishii, Tokyo (JP); Minoru Kadowaki, Tokyo (JP); Takaaki Kato, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,711

(22) PCT Filed: Sep. 13, 2013

(86) PCT No.: PCT/JP2013/074888
§ 371 (c)(1),
(2) Date: Mar. 19, 2015

(87) PCT Pub. No.: WO2014/050615
PCT Pub. Date: Apr. 3, 2014

(65) Prior Publication Data
US 2015/0231604 A1  Aug. 20, 2015

(30) Foreign Application Priority Data

Sep. 27, 2012 (JP) .................. 2012-214867

(51) Int. Cl.

| | |
|---|---|
| *B01J 23/00* | (2006.01) |
| *B01J 23/28* | (2006.01) |
| *B01J 23/30* | (2006.01) |
| *B01J 35/02* | (2006.01) |
| *B01J 37/00* | (2006.01) |
| *B01J 37/02* | (2006.01) |
| *B01J 37/04* | (2006.01) |
| *B01J 37/08* | (2006.01) |
| *C07C 253/24* | (2006.01) |
| *C07C 253/26* | (2006.01) |
| *C07C 255/07* | (2006.01) |
| *C07C 255/08* | (2006.01) |

(52) U.S. Cl.
CPC ........... *B01J 23/002* (2013.01); *B01J 23/28* (2013.01); *B01J 23/30* (2013.01); *B01J 37/0045* (2013.01); *B01J 37/04* (2013.01); *B01J 37/08* (2013.01); *B01J 37/088* (2013.01); *C07C 253/24* (2013.01); *C07C 253/26* (2013.01); *C07C 255/08* (2013.01); *B01J 35/023* (2013.01); *B01J 37/0009* (2013.01); *B01J 37/0236* (2013.01); *B01J 2523/00* (2013.01)

(58) Field of Classification Search
CPC ............................. B01J 23/28; C07C 253/26
See application file for complete search history.

(56) References Cited

U.S. PATENT DOCUMENTS

| | | | |
|---|---|---|---|
| 2008/0248947 A1 | 10/2008 | Zajac et al. | |
| 2010/0286432 A1* | 11/2010 | Tateno | B01J 23/002 558/330 |
| 2013/0253217 A1* | 9/2013 | Ishii | B01J 23/002 558/319 |

FOREIGN PATENT DOCUMENTS

| | | | | |
|---|---|---|---|---|
| JP | 2001-276618 A | 10/2001 | | |
| JP | 2002-219362 A | 8/2002 | | |
| JP | 2003-320248 A | 11/2003 | | |
| JP | 2007-216212 A | 8/2007 | | |
| JP | 2007-308423 A | 11/2007 | | |
| JP | 2007326036 A | * | 12/2007 | ............. B01J 23/28 |
| JP | 2010-523314 A | 7/2010 | | |
| JP | 2012-77039 A | 4/2012 | | |
| JP | 2012077039 A | * | 4/2012 | ........... C07C 253/24 |
| WO | WO 2012/090979 A1 | 7/2012 | | |

OTHER PUBLICATIONS

International Search Report, issued in PCT/JP2013/074888, dated Nov. 19, 2013.

(Continued)

*Primary Examiner* — Joseph R Kosack
(74) *Attorney, Agent, or Firm* — Birch, Stewart, Kolasch & Birch, LLP

(57) ABSTRACT

It is an object of the present invention to provide a composite oxide catalyst which can suppress the generation of $CO_2$ and CO and improve the yield of an unsaturated nitrile in a method for subjecting propane or isobutane to a vapor-phase catalytic ammoxidation reaction to produce a corresponding unsaturated nitrile, and a method for producing the composite oxide catalyst, and a method for producing an unsaturated nitrile using the composite oxide catalyst. A composite oxide catalyst used for a vapor-phase catalytic oxidation reaction or vapor-phase catalytic ammoxidation reaction of propane or isobutane, the composite oxide catalyst comprising a composite oxide represented by the following composition formula (1):

$$Mo_1V_aSb_bNb_cW_dZ_eO_n \qquad (1),$$

wherein the component Z is one or more element selected from the group consisting of La, Ce, Pr, Yb, Y, Sc, Sr, and Ba; a, b, c, d, e, and n represent atomic ratios of the elements; and $0.1 \le a < 0.2$, $0.15 \le b \le 0.5$, $0.01 \le c \le 0.5$, $0 \le d \le 0.4$, $0 \le e \le 0.2$, and $0.60 < a/b < 1.00$.

8 Claims, No Drawings

(56) References Cited

OTHER PUBLICATIONS

Watanabe et al., "Comparative Study on the Catalytic Performance of Single-Phase Mo—V—O-Based Metal Oxide Catalysts in Propane Ammoxidation to Acrylonitrile", Industrial & Engineering Chemistry Research, 2006, vol. 45, No. 2, pp. 607-614.
Supplementary European Search Report dated Jan. 14, 2016, in European Patent Application No. 13841273.9.

* cited by examiner

COMPOSITE OXIDE CATALYST, METHOD FOR PRODUCING THE SAME, AND METHOD FOR PRODUCING UNSATURATED NITRILE

TECHNICAL FIELD

The present invention relates to a composite oxide catalyst, a method for producing the composite oxide catalyst, and a method for producing an unsaturated nitrile using the composite oxide catalyst.

BACKGROUND ART

At the present day, an unsaturated nitrile which is generally available commercially is mainly produced industrially by the catalytic ammoxidation reaction of olefin, ammonia, and oxygen. On the other hand, in recent years, a method for subjecting an alkane such as propane or isobutane as a raw material in place of the olefin to a vapor-phase catalytic ammoxidation reaction to produce a corresponding unsaturated nitrile has attracted people's attention. Various catalysts used in the case have also been proposed.

Patent Literature 1 describes a catalyst wherein a composite metal oxide containing Mo, V, Nb, and B is supported by 20 to 60% by mass of silica in terms of $SiO_2$ based on the total mass of an oxide and silica, as a catalyst for the vapor-phase catalytic oxidation or vapor phase catalytic ammoxidation of propane or isobutane.

Patent Literature 2 describes a silica-supported catalyst used when propane or isobutane is subjected to a vapor-phase catalytic ammoxidation reaction to produce an unsaturated nitrile, or the propane or isobutane is subjected to a vapor-phase catalytic oxidation reaction to produce an unsaturated carboxylic acid, wherein the silica-supported catalyst has a specific metal component composition, a silica content rate, and a pore volume.

Generally, when focus is on the ratio of V/Sb in an MoVSbOx type ammoxidation catalyst, V is more than Sb. Such a ratio has been well known in an ammoxidation catalyst synthesized by hydrothermal synthesis or the like (for example, see Non Patent Literature 1). Therefore, also in an MoV type ammoxidation composite oxide catalyst prepared by a method except the hydrothermal synthesis, the amount of V to Sb has been adjusted so as not to decrease the amount if possible or so as to increase the amount.

Patent Literatures 3 shows a catalyst having an improved reaction yield and catalyst life. However, a large amount of V is still used. On the other hand, in the actual reaction, it has been known that Mo in an active structure forms a complex with water generated by a catalytic reaction or a side reaction, which causes the escaping of Mo. In the case of an MoV composite crystal, the escaping of Mo relatively increases V in the composite crystal to excessively increase the activity to the raw material.

CITATION LIST

Patent Literature

Patent Literature 1: Japanese Patent Laid-Open No. 2001-276618
Patent Literature 2: Japanese Patent Laid-Open No. 2002-219362
Patent Literature 3: International Publication No. W02012-090979

Non Patent Literature

Non Patent Literature 1: Ind. Eng. Chem. Res., Vol. 45, NO. 2, 2006 P 607-614

SUMMARY OF INVENTION

Technical Problem

A further improvement in a yield has been required for industrial production from the above-mentioned reasons. Even if the catalysts described in the above-mentioned Patent Literatures 1 to 3 are used, many by-products such as carbon dioxide ($CO_2$) and carbon monoxide (CO) are generated, which brings about an insufficient yield of the unsaturated nitrile. $CO_2$ and CO are compounds having no, application. The suppression of the generation thereof leads also to effective utilization of the raw material.

The present invention has been accomplished in view of the above-mentioned problems. It is an object of the present invention to provide a composite oxide catalyst which can suppress the generation of $CO_2$ and CO and improve the yield of an unsaturated nitrile in a method for subjecting propane or isobutane to a vapor-phase catalytic ammoxidation reaction to produce a corresponding unsaturated nitrile, and a method for producing the composite oxide catalyst, and a method for producing an unsaturated nitrile using the composite oxide catalyst.

Solution to Problem

The present inventors carried out investigations into the above-mentioned problems. The present inventors found that vanadium (V) is involved in the generation of $CO_2$ and CO. It has become clear that $CO_2$ and CO are generated in large amounts because excess V which is not complexed with another metal such as Mo or Nb is present according to a certain factor in the conventional catalyst. It was also found that Mo escapes during the reaction to relatively increase V in the composite oxide catalyst and to excessively increase the activity to the raw material, thereby speeding side reaction generation. On the other hand, a decrease in V in the composite oxide catalyst may cause deviation from a metal composition of active species which have been considered hitherto, and excessively decrease the activity to the raw material. Therefore, the decrease in V in the composite oxide catalyst has not been considered.

Then, in order to solve the above-mentioned problems, the present inventors have made eager investigation to achieve a low V composition to Mo and an improvement in a yield. The present inventors found that when a ratio of Mo to V and a ratio of V to Sb fall into a specific range, performance is improved while excessive V is decreased. As a result, the present invention has been completed.

That is, the present invention is as follows.

[1]
A composite oxide catalyst used for a vapor-phase catalytic oxidation reaction or vapor-phase catalytic ammoxidation reaction of propane or isobutane, the composite oxide catalyst comprising a composite oxide represented by the following composition formula (1):

$$Mo_1V_aSb_bNb_cW_dZ_eO_n \qquad (1),$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$.

[2]

The composite oxide catalyst according to [1], further comprising 20 to 70% by mass of silica in terms of $SiO_2$.

[3]

A method for producing a composite oxide catalyst comprising a composite oxide represented by the following composition formula (1):

$$Mo_1V_aSb_bNb_cW_dZ_eO_n \quad (1),$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$, the method comprising:

(I) a raw material blending step of preparing a raw material blending liquid which comprises Mo, V, Sb, Nb, W, and Z and in which $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$ for the atomic ratios;

(II) a drying step of drying the raw material blending liquid to obtain a dried powder;

(III) a calcining step of calcining the dried powder to obtain a calcined body; and (IV) a projection substance removing step of removing a projection substance present on a particle surface of the calcined body.

[4]

The method for producing the composite oxide catalyst according to [3], wherein the raw material blending step (I) comprising the steps of:

(a) preparing an aqueous mixed liquid containing Mo, V, Sb, and the component Z;

(b) adding silica sol and hydrogen peroxide water to the aqueous mixed liquid obtained in the (a) step;

(c) mixing the solution obtained in the (b) step with an aqueous solution containing Nb, dicarboxylic acid, and hydrogen peroxide water, and a W-containing compound; and (d) adding a powder silica-containing suspension liquid to the solution obtained in the (c) step to age the solution.

[5]

A method for producing a corresponding unsaturated nitrile by subjecting propane or isobutane to a vapor-phase catalytic oxidation reaction or a vapor-phase catalytic ammoxidation reaction, the corresponding unsaturated nitrile being derived from the propane and isobutene, wherein the composite oxide catalyst according to [1] or [2] is used.

Advantageous Effects of Invention

The present invention can realize a composite oxide catalyst which can suppress the generation of $CO_2$ and CO and improve the yield of an unsaturated nitrile. The present invention can also realize a method for producing a composite oxide catalyst wherein the composite oxide catalyst can be easily produced at low cost. Further, a method for producing an unsaturated nitrile which can suppress the generation of $CO_2$ and CO and improve the yield of an unsaturated nitrile can be realized by using the composite oxide catalyst.

DESCRIPTION OF EMBODIMENTS

Hereinafter, a mode for carrying out the present invention (hereinafter, merely referred to as "present embodiment") will be described in detail. The following present embodiment is given in order to illustrate the present invention. The present invention should not be construed to be limited to the following contents. The present invention may be carried out while making appropriate modification within the scope of the invention.

[Composite Oxide Catalyst]

A composite oxide catalyst of the present embodiment is used for a vapor-phase catalytic oxidation reaction or vapor-phase catalytic ammoxidation reaction of propane or isobutane, and comprises a composite oxide represented by the following composition formula (1):

$$Mo_1V_aSb_bNb_cW_dZ_eO_n \quad (1)$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$.

In the composite oxide catalyst, from the viewpoint of preventing the decomposition reaction of a generated unsaturated nitrile, it is preferable that the component Z is uniformly distributed in a catalyst particle. The term "uniformly" means that the distribution of the component Z is not disproportionate in the catalyst particle. Preferably, the term "uniformly" means that 80% or more (percentage by mass) of the oxide particles containing the component Z are present in the catalyst particle as fine particles each having a particle diameter of 1 μm or less. When the composite oxide catalyst contains silica, from the viewpoint of uniformity, a dispersion value (a value obtained by dividing a standard deviation by a mean value) of a signal strength ratio of the component Z to Si, at the time of composition analysis of a cross-section of the catalyst particle is preferably in the range of 0 to 0.5, more preferably in the range of 0 to 0.4, and still more preferably in the range of 0 to 0.3. Herein, the dispersion value of the signal strength ratio is represented by "Dx" to be described later.

In the composite oxide catalyst of the present embodiment, from the viewpoint of improving the yield of the unsaturated nitrile, it is important to set an atomic ratio (a) of V to Mo and a ratio (a/b) of V to Sb to the range of $0.1 \leq a < 0.2$ and the range of $0.60 < a/b < 1.00$, respectively. From the present inventors' investigation, it has become clear that excessively surplus V which is not complexed well with the other metal components is present in a conventional catalyst, and the presence of the excessively surplus V becomes a factor for generating $CO_2$ and CO and for decreasing the yield of the unsaturated nitrile. Then, as a result of focus on the ratio of Mo to V and the ratio of V to Sb, and continued eager investigation, it was clear that the excessively surplus V can be suppressed by setting the atomic ratio of V to Mo and the ratio of V to Sb to the range of $0.1 \leq a < 0.2$ and the range of $0.60 < a/b < 1.00$, respectively. Thus, the excessively surplus V is suppressed, and thereby the generation of $CO_2$ and CO can be suppressed without decreasing the activity to the raw material, and the yield of the unsaturated nitrile can be improved.

The present inventors carried out investigations, and found that the yield of a target is improved when the atomic ratio of V to Mo and the ratio of V to Sb fall into the above-mentioned specific ranges. When the atomic ratio of V to Mo is in the range of $0.1 \leq a < 0.2$, a place where Mo should be essentially present is substituted by V, to increase the ratio of V in a crystal structure required for propane activity, which improves activity. When the ratio of V to Sb is in the range of $0.60 < a/b < 1.00$, V and Mo is unlikely to be oxidized during catalyst calcining, which suppresses the deposition of the oxides of V and Mo. Thereby, it is presumed that the amount of active species in the composite oxide catalyst is relatively increased, to improve the selectivity of a target product. From the above-mentioned viewpoint, a is preferably in the range of $0.12 \leq a < 0.2$, and more preferably in the range of $0.13 \leq a < 0.2$. a/b is preferably in the range of $0.60 < a/b < 0.95$, and more preferably in the range of $0.60 < a/b < 0.85$. a and a/b are in the above-mentioned ranges, and thereby the generation of $CO_2$ and CO can be further suppressed, and the yield of the unsaturated nitrile can be further improved.

b is in the range of $0.15 \leq b \leq 0.5$, preferably in the range of $0.15 \leq b \leq 0.4$, and more preferably in the range of $0.15 \leq b \leq 0.3$. c is in the range of $0.01 \leq c \leq 0.5$, preferably in the range of $0.01 \leq c \leq 0.4$, and more preferably in the range of $0.01 \leq c \leq 0.35$. Further, d is in the range of $0 \leq d \leq 0.4$, preferably in the range of $0 \leq d \leq 0.3$, and more preferably in the range of $0 \leq d \leq 0.25$. Further, e is in the range of $0 \leq e \leq 0.2$, preferably in the range of $0 \leq e \leq 0.15$, and more preferably in the range of $0 \leq e \leq 0.1$. b, c, d, and e are in the above-mentioned ranges, and thereby the generation of $CO_2$ and CO can be further suppressed, and the yield of the unsaturated nitrile can be further improved.

n represents a rate of an oxygen atom, and is a numerical value decided by a, b, c, d, and e. Z is one or more element selected from the group consisting of La, Ce, Pr, Yb, Y, Sc, Sr, and Ba. Among them, Yb, Y, La, and Ce are preferable, and Ce is more preferable.

Preferably, the composite oxide catalyst of the present embodiment further contains 20 to 70% by mass of silica in terms of $SiO_2$ based on the total mass of a catalyst containing a composite oxide and silica, more preferably 40 to 65% by mass of silica, and still more preferably 40 to 60% by mass of silica. The content of silica is 20% by mass or more, and thereby the strength of the catalyst tends to be further improved. The content of silica is 70% by mass or less, and thereby the catalyst tends to have higher activity.

A method for measuring a concentration of a catalyst-constituting element is not particularly limited. A general method for measuring a metal concentration can be adopted. For example, X-ray fluorescence analysis (XRF) can be used. When a concentration of a metal in a solid particle catalyst is measured, the XRF can be suitably used from the viewpoints of simplicity of measurement and precision of quantitative determination or the like. When a slight amount of metal is analyzed, a catalyst is dissolved in an appropriate solution, and the amount can be determined by ICP or atomic absorption using the solution liquid. When the amounts of carbon, hydrogen, and nitrogen are desired to be determined, CHN analysis can be suitably used. The above Dx can be obtained by EPMA or the like.

[Method for Producing Composite Oxide Catalyst]

A method for producing a composite oxide catalyst of the present embodiment is a method for producing a composite oxide catalyst comprising a composite oxide represented by the following composition formula (1):

$$Mo_1V_aSb_bNb_cW_dZ_eO_n \qquad (1),$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$, the method comprising:

(I) a raw material blending step of preparing a raw material blending liquid which comprises Mo, V, Sb, Nb, W, and Z such that $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 1.00$ for the atomic ratios;

(II) a drying step of drying the raw material blending liquid to obtain a dried powder;

(III) a calcining step of calcining the dried powder to obtain a calcined body; and (IV) a projection substance removing step of removing a projection substance present on a particle surface of the calcined body.

[(I) Raw Material Blending Step]

In the raw material blending step of the present embodiment, for example, the raw material blending liquid is prepared such that an atomic ratio a of V, an atomic ratio b of Sb, an atomic ratio c of Nb, an atomic ratio d of W, and an atomic ratio e of Z to one atom of Mo were in the ranges of $0.1 \leq a < 0.2$, $0.15 \leq b\ 5 \leq 0.5$, $0.01 \leq c \leq 0.5$, $0 \leq d \leq 0.4$, and $0 \leq e \leq 0.2$, respectively, and $0.60 < a/b < 1.00$. The composition ratio is set to a value different from the composition ratio of the composite oxide catalyst finally obtained. This is because a projection substance of a catalyst to be described later has a composition different from that of the main body of the catalyst; the composition ratio of the whole catalyst is also changed by removing the projection substance from the main body of the catalyst; and the composition ratio is set while taking the change into account in the raw material blending step. In the present specification, the "projection substance" means an object oozing and/or adhering on the surface of a calcined body obtained by final calcination to be described later. The "projection substance" means an object projecting from the surface of the calcined body or adhering on the surface.

(Preparation of Catalyst)

A raw material for Mo is not particularly limited. Specifically, ammonium heptamolybdate [$(NH4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentachloride [$MoCl_5$] or the like can be used. Among them, ammonium heptamolybdate [$(NH_4)_6Mo_7O_{24} \cdot H_2O$] is particularly preferable.

A raw material for V is not particularly limited. Specifically, ammonium metavanadate [$NH_4VO_3$], vanadium pentoxide [$V_2O_5$], and vanadium chloride [$VCl_4$, $VCl_3$] or the like can be used. Among them, ammonium metavanadate [$NH_4VO_3$] is particularly preferable.

A raw material for Sb is not particularly limited. Specifically, antimony oxide [$Sb_2O_3$, $Sb_2O_5$], antimonious acid [$HSbO_2$], antimonic acid [$HSbO_3$], ammonium antimonate [$(NH_4)SbO_3$], antimony chloride [$Sb_2Cl_3$], and an organic acid salt such as a tartrate of antimony, and metal antimony or the like can be used. Among them, diantimony trioxide [$Sb_2O_3$] is particularly preferable.

A raw material for Nb is not particularly limited. Specifically, niobic acid, an inorganic niobate and an organic niobate can be used. Particularly, niobic acid is preferable. Niobic acid is represented by $Nb_2O_5 \cdot nH_2O$, and is denoted also as niobium hydroxide or niobium oxide hydrate. Further, a Nb raw material solution in which a molar ratio of dicarboxylic acid/niobium is 1 to 4 is preferably used as the raw material for Nb. As the dicarboxylic acid, oxalic acid is preferable.

A raw material for W is not particularly limited. Specifically, a tungsten salt such as an ammonium salt, a nitrate, a carboxylate, ammonium carboxylate, a peroxocarboxylate, ammonium peroxocarboxylate, a halogenated ammonium salt, a halide, acetylacetonate, an alcoxide, a triphenyl compound, a polyoxometalate, ammonium polyoxometalate; tungsten trioxide, tungsten dioxide, tungstic acid, an ammonium metatungstate aqueous solution, ammonium paratungstate, tungstosilicic acid, silicotungstomolybdic acid, and tungstosilicic acid or the like can be used. Among them, the ammonium metatungstate aqueous solution is preferable.

A raw material for Z (one or more element selected from the group consisting of La, Ce, Pr, Yb, Y, Sc, Sr, and Ba) is not particularly limited, so long as the raw material for Z contains any of these elements. Compounds containing any of these elements, and a material in which metal of any of these elements is solubilized by an appropriate reagent can be used. As the compound containing any of these elements, ordinarily, an ammonium salt, a nitrate, a carboxylate, ammonium carboxylate, a peroxocarboxylate, ammonium peroxocarboxylate, a halogenated ammonium salt, a halide, acetylacetonate, an alcoxide or the like can be used. Among them, an aqueous raw material such as a nitrate or a carboxylate is preferably used.

In blending the raw materials, the dissolving procedure, mixing procedure, or dispersing procedure of the raw materials of the catalyst-constituting elements is not particularly limited. The raw materials may be dissolved, mixed, or dispersed in the same aqueous medium. Alternatively, the raw materials may be individually dissolved, mixed, or dispersed in aqueous media, and then the aqueous media may be mixed. Heating and/or stirring may be performed if needed.

When the composite oxide catalysts in the present embodiment is a catalyst containing silica, and preferably a silica-supported catalyst supported by silica, the raw material blending liquid is preferably prepared so as to contain a raw material for silica. The raw material for silica is not particularly limited. Specifically, silica sol can be used. Powder silica can be used either partially or entirely as the raw material for silica.

The raw material blending step in the present embodiment preferably comprises the steps of:

(a) preparing an aqueous mixed liquid containing Mo, V, Sb, and the component Z;

(b) adding silica sol and hydrogen peroxide water to the aqueous mixed liquid obtained in the (a) step;

(c) mixing the solution obtained in the (b) step with an aqueous solution containing Nb, dicarboxylic acid, and hydrogen peroxide water, and a W-containing compound; and (d) adding a powder silica-containing suspension liquid to the solution obtained in the (c) step to age the solution. Thereby, metal valences of metal species tend to become more proper in the stage before calcining.

Hereinafter, the above-mentioned raw material blending step will described using an example in which a raw material blending liquid of a silica-supported catalyst containing an Mo-containing compound, a V-containing compound, an Sb-containing compound, an Nb-containing compound, a W-containing compound, and a Z-containing compound is prepared using water as a solvent and/or a dispersion medium. Note that the raw material blending step is not limited thereto.

The Mo-containing compound, the V-containing compound, the Sb-containing compound, and the Z-containing compound are added to water, and heated to prepare an aqueous mixed liquid (A). A heating temperature and a heating time when the aqueous mixed liquid (A) is prepared are preferably adjusted such that raw material compounds can be sufficiently dissolved. The heating temperature is preferably 70° C. to 100° C. The heating time is preferably 30 minutes to 5 hours. At this time, the aqueous mixed liquid (A) is preferably stirred such that the raw materials are likely to be dissolved. At this time, the interior of the vessel may be an air atmosphere. However, from the viewpoint of adjusting the oxidation number of the obtained composite oxide catalyst, the interior of the vessel may be a nitrogen atmosphere. The state of the aqueous mixed liquid (A) after heating is ended is defined as an aqueous mixed liquid (A'). The temperature of the aqueous mixed liquid (A') is preferably held at 20° C. or more and 80° C. or less, and more preferably 40° C. or more and 80° C. or less. The temperature of the aqueous mixed liquid (A') is 20° C. or more, and thereby the deposition of the metal species dissolved in the aqueous mixed liquid (A') tends to be unlikely to occur.

Then, silica sol is added to the aqueous mixed liquid (A) or the aqueous mixed liquid (A') after heating is ended. The silica sol functions as a carrier. A temperature when the silica sol is added is preferably 80° C. or less. When the silica sol is added at 80° C. or less, the stability of the silica sol is comparatively high, which tends to suppress the gelling of the raw material blending liquid. The silica sol may be added when aging to be described later is started, in the middle of aging, or just before the raw material blending liquid is dried. The silica sol is preferably added to the aqueous mixed liquid (A'). Further, from the viewpoint of adjusting the oxidation number of the obtained composite oxide, an appropriate amount of hydrogen peroxide water is preferably added to the aqueous mixed liquid (A') if needed. The hydrogen peroxide water may be added to the aqueous mixed liquid (A') itself. The hydrogen peroxide water may be added in the middle of the blending of the aqueous mixed liquid (A'), or after or before the silica sol is added. At this time, from the viewpoint of adjusting the oxidation number of the obtained composite oxide catalyst to a proper range, as for the amount of the hydrogen peroxide water to be added, $H_2O_2/Sb$ (molar ratio) is preferably 0.01 to 5, more preferably 0.5 to 3, and still more preferably 1 to 2.5.

A heating temperature and a heating time after the hydrogen peroxide water is added to the aqueous mixed liquid (A') are preferably adjusted such that a liquid phase oxidation reaction due to the hydrogen peroxide water can sufficiently proceed. The heating temperature is preferably 30° C. to 70° C. The heating time is preferably 5 minutes to 4 hours. Similarly, the rotation number of stirring during heating can be adjusted to an appropriate rotation number in which the liquid phase oxidation reaction due to the hydrogen peroxide water is likely to proceed. From the viewpoint of causing the liquid phase oxidation reaction due to the hydrogen peroxide water to sufficiently proceed, a stirring state is preferably kept during heating. The aqueous mixed liquid prepared thus is defined as (A").

Next, the Nb-containing compound and the dicarboxylic acid are heated while stirring in water to prepare a mixed liquid ($B_0$). Examples of the dicarboxylic acid include oxalic acid [$(COOH)_2$]. Then, hydrogen peroxide water is preferably added to the mixed liquid ($B_0$) to prepare an aqueous mixed liquid (C). At this time, from the viewpoints of forming a complex with the Nb-containing compound to stabilize the Nb-containing compound in a dissolved state, of properly adjusting the oxidation/reduction state of the catalyst-constituting element, and of making the catalyst performance of the obtained catalyst proper, $H_2O_2/Nb$ (molar ratio) is preferably 0.5 to 20, and more preferably 1 to 10.

Then, depending on a composition to be targeted, the aqueous mixed liquid (A"), the aqueous mixed liquid (C), the W-containing compound, and the powder silica are suitably mixed to obtain an aqueous mixed liquid (D). Subsequently, the obtained aqueous mixed liquid (D) is subjected to aging treatment to obtain a raw material blending liquid. From the viewpoint of making the catalyst performance of the obtained catalyst proper, the powder silica used here is preferably added to the solution obtained by mixing the aqueous mixed liquid (A"), the aqueous mixed liquid (C), and the W-containing compound. The powder silica can be added as it is. More preferably, the powder silica is preferably added as a liquid in which powder silica is dispersed in water, i.e., a powder silica-containing suspension liquid. The concentration of the powder silica in the powder silica-containing suspension liquid at this time is preferably 1 to 30% by mass, and more preferably 3 to 20% by mass. The concentration of the powder silica is 1% by mass or more, and thereby the distorted shape of the catalyst particle caused by the low viscosity of a slurry tends to be able to be suppressed. The occurrence or the like of a depression in the catalyst particle also tends to be able to be suppressed. The concentration of the powder silica is 30% by mass or less, and thereby the gelling of the raw material blending liquid and clogging a pipeline caused by the high viscosity of the raw material blending liquid tend to be able to be avoided, making it possible to easily obtain a dried powder. Further, the catalyst performance also tends to be further improved.

The aging of the aqueous mixed liquid (D) means that the aqueous mixed liquid (D) is left standstill or stirred for a predetermined time. An aging time is preferably 90 minutes or more and 50 hours or less, and more preferably 90 minutes or more and 6 hours or less. The aging time is within the above-mentioned range, and thereby the aqueous mixed liquid (D) having a suitable oxidation/reduction state (electric potential) is likely to be formed, which tends to further improve the catalyst performance of the obtained composite oxide. Here, when the composite oxide catalyst is industrially produced after drying by a spray dryer, the treatment speed of the spray dryer is ordinarily rate-controlling. A long time is required until the spray drying of the whole mixed liquid is ended after a part of the aqueous mixed liquid (D) is spray-dried. In the meantime, the aging of the aqueous mixed liquid which is not subjected to spray drying treatment is continued. Therefore, the aging time includes not only an aging time before drying in a step (II) to be described later but also a time from the starting to ending of drying. From the viewpoint of preventing the condensation of an Mo component and the deposition of metal oxides due to V and the other metal species or a plurality of metals, an aging temperature is preferably 25° C. or more. From the viewpoint of preventing the hydrolysis of a complex containing Nb and hydrogen peroxide from excessively occurring to form a slurry in a preferable form, the aging temperature is preferably 65° C. or less, more preferably 25° C. or more and 65° C. or less, and still more preferably 45° C. or more and 60° C. or less. The catalyst can be further reduced during calcining by extending the aging time, raising the aging temperature or the like, or performing the extending and the raising in combination. The present inventors have studied diligently, and, as a result, found that the reduction rate of the catalyst after calcining and the oxidation-reduction potential of the slurry have a certain correlation. If the oxidation-reduction potential of the slurry increases, the catalyst after calcining becomes oxidative. If the oxidation-reduction potential of the slurry decreases, the catalyst after calcining becomes reductive. Therefore, the oxidation-reduction potential of the slurry is preferably 400 to 600 mV, more preferably 450 to 550 mV, and still more preferably 470 to 510 mV.

[(II) Drying Step]

The drying step of the present embodiment is a step of drying the raw material blending liquid to obtain a dried powder. The drying can be performed by a known method. For example, the drying can be performed by spray drying or evaporation to dryness. When a fluidized-bed reaction method is adopted in the vapor-phase catalytic oxidation reaction or the vapor-phase catalytic ammoxidation reaction, a dried powder in a minute sphere state is preferably obtained from the viewpoint of causing flowability within a reactor to a preferable state or the like, and therefore, the spray drying is preferably adopted. The atomization in the spray drying method may be carried out by a centrifugation method, a two-fluid nozzle method, or a high-pressure nozzle method. Air heated by steam or an electric heater or the like may be used as the heat source for drying.

A spray velocity, a velocity of the raw material blending liquid to be fed, and a rotation number of an atomizer in the case of the centrifugation method, or the like are preferably adjusted such that the size of the obtained dried powder is suitable. The mean particle diameter of the dried powder is preferably 35 to 75 μm, more preferably 40 to 70 μm, and still more preferably 45 to 65 μm. The mean particle diameter does not vary greatly even after calcining.

[(III) Calcining Step]

The calcining step of the present embodiment is a step of calcining a dried powder to obtain a calcined body. For example, a rotary furnace (rotary kiln) can be used as a calcining apparatus for calcining the dried powder. The shape of a calcining machine for calcining the dried powder therein is not particularly limited. The shape is preferably a tube shape (calcining tube) from the viewpoint of the fact that continuous calcining can be carried out, and particularly preferably a cylindrical shape. From the viewpoint of being likely to adjust a calcining temperature to a preferable rising temperature pattern or the like, a heating method is preferably an outer heating method. An electric furnace can be suitably used. The size and quality or the like of the calcining tube can be appropriately selected according to a calcining condition or a production amount.

The calcination is desirably performed in two steps in the calcining step. When the first calcination is defined as preliminary calcination and the subsequent calcination is defined as final calcination, it is preferable that the preliminary calcination is performed in the temperature range of 250 to 400° C., and the final calcination is performed in the temperature range of 450 to 700° C. The preliminary calcination and the final calcination may be continuously carried out. The final calcination may be carried out after the preliminary calcination is completed once. The preliminary calcination and the final calcination may be respectively divided into several steps.

The calcination may be performed in an atmospheric environment or in a circulation of air. However, from the viewpoint of adjusting the composite oxide catalyst to a preferable oxidation/reduction state, at least a part of the calcination is preferably carried out while an inert gas which is substantially free from oxygen such as nitrogen is circulated. When the calcination is performed by a batch method, the amount of the inert gas to be supplied is preferably 50 NL/hr or more per 1 kg of the dried powder from the viewpoint of adjusting the composite oxide catalyst to a preferable oxidation/reduction state, more preferably 50 to 5000 NL/hr, and still more preferably 50 to 3000 NL/hr. Here, "NL" means a volume of a gas measured under standard temperature and pressure conditions, i.e., at 0° C. under a pressure condition of 1 atmosphere.

In the method for producing the composite oxide catalyst of the present embodiment, the reduction rate of the preliminary calcined body is preferably 7 to 15%, more preferably 8 to 12%, and still more preferably 9 to 12%. The reduction rate is within this range, and thereby, for example, the yield is further improved in the viewpoint of catalyst production. Specific examples of a method for controlling the reduction rate to a desired range include a method for changing the preliminary calcination temperature, a method for adding an oxidizing component such as oxygen into an atmosphere during calcining, or a method for adding a reducing component into an atmosphere during calcining. They may be combined.

[(IV) Projection Substance Removing Step]

The projection substance removing step of the present embodiment is a step of removing a projection substance which is present on the particle surface of the calcined body. Many projection substances are projecting oxide crystals and other impurities. Particularly, in the case of the calcined body containing a plurality of metals, the oxide having a composition different from that of the crystal forming a large part of the calcined body may be formed in such a shape that the oxide oozes out from the main part of the calcined body. Because such a projection substance becomes a factor of decreasing flowability, the projection substance should be removed from the catalyst surface. When the projection substance is removed on a gram scale, the following apparatus can be used. That is, a perpendicular tube can be used, wherein a perforated plate having one or more holes is provided in a bottom part, and a paper filter is provided in an upper part. The calcined bodies are put in the perpendicular tube, and air is circulated from a lower part. Therefore, an air current flows from each hole, to urge the contact of the calcined bodies, thereby removing the projection substances.

[Method for Producing Unsaturated Nitrile]

A method for producing an unsaturated nitrile of the present embodiment is a method for producing a corresponding unsaturated nitrile by subjecting propane or isobutane to a vapor-phase catalytic oxidation reaction or a vapor-phase catalytic ammoxidation reaction, the corresponding unsaturated nitrile being derived from the propane and isobutene, wherein the composite oxide catalyst of the present embodiment is used. Hereinafter, there will be described a method for subjecting propane to a vapor-phase catalytic ammoxidation reaction in a state where propane, ammonia, and an oxygen-containing gas are brought into contact with the composite oxide catalyst of the present embodiment with which a reactor is filled, to produce acrylonitrile.

(Raw Materials)

Propane and ammonia as raw materials are not necessarily highly pure but those of industrial grade such as propane containing 3 vol % or less of impurities, for example, ethane, ethylene, n-butane, and isobutane, and ammonia containing about 3 vol % or less of impurities, for example, water can be used. Examples of the oxygen-containing gas include, but are not particularly limited to, air, air enriched with oxygen, pure oxygen, or a gas such as these diluted with inert gas such as helium, argon, carbon dioxide or nitrogen, or water vapor. When the gases are used on an industrial scale, among them, the air is preferably used from simplicity.

(Reaction Condition)

The vapor-phase catalytic oxidation reaction of propane or isobutane is not particularly limited. Specifically, the vapor-phase catalytic oxidation reaction can be performed under the following conditions. A molar ratio of oxygen to be supplied for the reaction to propane or isobutane is preferably 0.1 to 6, and more preferably 0.5 to 4. A reaction temperature is preferably 300 to 500° C., and more preferably 350 to 500° C. A reaction pressure is preferably $5 \times 10^4$ to $5 \times 10^5$ Pa, and more preferably $1 \times 10^5$ to $3 \times 10^5$ Pa. A contact time is preferably 0.1 to 10 (sec·g/cm$^3$), and more preferably 0.5 to 5 (sec·g/cm$^3$). The reaction conditions are within the above-mentioned ranges, and thereby the generation of $CO_2$ and CO tends to be able to be further suppressed, and the yield of the unsaturated nitrile tends to be able to be further improved.

In the present embodiment, the contact time is defined by the following formula.

Contact Time (sec·g/cm$^3$)=$(W/F) \times 273/(273+T)$

Here, W, F, and T are defined as follows:

W=filled amount (g) of a catalyst;

F=flow rate (N cm$^3$/sec) of a raw material mixed gas under standard conditions (0° C., $1.013 \times 10^5$ Pa); and T=reaction temperature (° C.).

The vapor-phase catalytic ammoxidation reaction of propane or isobutane using the composite oxide catalyst of the present embodiment is not particularly limited. Specifically, the vapor-phase catalytic ammoxidation reaction can be performed under the following conditions. A molar ratio of oxygen to be supplied for the reaction to propane or isobutane is preferably 0.1 to 6, and more preferably 0.5 to 4. A molar ratio of ammonia to be supplied for the reaction to propane or isobutane is preferably 0.3 to 1.5, and more preferably 0.7 to 1.2. A reaction temperature is preferably 350 to 500° C., and more preferably 380 to 470° C. A reaction pressure is preferably $5 \times 10^4$ to $5 \times 10^5$ Pa, and more preferably $1 \times 10^5$ to $3 \times 10^5$ Pa'. A contact time is preferably 0.1 to 10 (sec·g/cm$^3$), and more preferably 0.5 to 5 (sec·g/cm$^3$). The reaction conditions are within the above-mentioned ranges, and thereby the generation of $CO_2$ and CO tends to be able to be further suppressed, and the yield of the unsaturated nitrile tends to be able to be further improved.

Conventional methods such as a fixed bed method, a fluidized bed method, and a moving bed method can be adopted as a reaction method in the vapor-phase catalytic oxidation reaction and the vapor-phase catalytic ammoxidation reaction. Among them, due to easiness of removal of a reaction heat, a fluidized bed reactor is preferable. The vapor-phase catalytic ammoxidation reaction may either be a single current system or a recycle system.

EXAMPLES

Hereinafter, the present embodiment will be described in more detail with reference to Examples and Comparative Examples, but the present embodiment is not limited to these Examples.

[Yield of Acrylonitrile (Unsaturated Nitrile)]

In Examples and Comparative Examples, the yield of acrylonitrile is followed by the following definition. The molar number of the generated acrylonitrile was measured by previously analyzing a gas of acrylonitrile having a known concentration with gas chromatography (GC: manufactured by Shimadzu Corporation, product name: GC2014) to obtain a calibration curve, and thereafter injecting a certain amount of gas generated in an ammoxidation reaction into the GC.

Yield of Acrylonitrile (%)=(Molar Number of Generated Acrylonitrile)/(Molar Number of Supplied Propane)×100

[Yield of CO$_2$ and CO]

In Examples and Comparative Examples, the yield of CO$_2$ and CO is followed by the following definition. The molar number of the generated CO$_2$ and CO was measured by previously analyzing a CO$_2$ gas and a CO gas each having a known concentration with gas chromatography (GC: manufactured by Shimadzu Corporation, product name: GC2014) to obtain calibration curves, and then injecting a certain amount of gas generated in an ammoxidation reaction into the GC.

Yield of CO$_2$ or CO (%)=(Molar Number of Generated CO$_2$ or CO)/{(Molar Number of Supplied Propane or Isobutane)×(Carbon Number of Propane or Isobutane)}×100

Example 1

(Preparation of Dried Powder)

A dried powder (D$_1$) was produced as follows.

To 1.771 g of water, 340.5 g of ammonium heptamolybdate [(NH$_4$)$_6$Mo$_7$O$_{24}$.4H$_2$O], 46.9 g of ammonium metavanadate [NH$_4$VO$_3$], 66.2 g of diantimony trioxide [Sb$_2$O$_3$], and 4.2 g of cerium nitrate [Ce(NO$_3$)$_3$.6 H$_2$O] were added and heated at 95° C. for 1 hour with stirring, to prepare an aqueous raw material liquid (A$_1$).

To 257.6 g of a niobium mixed liquid (B$_0$) in which a molar ratio of oxalic acid/niobium was 2.5, 40 g of hydrogen peroxide water containing 30% by mass of H$_2$O$_2$ was added, and mixed at room temperature for 10 minutes with stirring to prepare an aqueous raw material liquid (B$_1$).

After the obtained aqueous raw material liquid (A$_1$) was cooled to 70° C., 564.7 g of silica sol containing 34.0% by mass of SiO$_2$ was added thereto, and 80 g of hydrogen peroxide water containing 30% by mass of H$_2$O$_2$ was further added thereto. Then, the resultant mixture was continuously stirred for 30 minutes at 55° C. Next, the aqueous raw material liquid (B$_1$), 26.5 g of an ammonium metatungstate aqueous solution (concentration: 50%), and a dispersion liquid obtained by dispersing 192 g of powder silica in 1728 g of water were sequentially added to the aqueous raw material liquid (A$_1$), and the resultant mixture was then stirred and aged at 50° C. for 2.5 hours to obtain a slurry aqueous mixed liquid (C$_1$) as a raw material blending liquid.

The obtained aqueous mixed liquid (C$_1$) was supplied to a centrifugal spray dryer (a drying heat source is air; and the same will apply hereafter) and dried to obtain a dried powder (D$_1$) in a minute sphere state. Temperatures at an inlet and an outlet of the dryer were respectively 210° C. and 120° C.
(Classification Operation)

The obtained dried powder (D$_1$) was classified using a sieve having an opening of 25 μm to obtain a dried powder (E$_1$) as a classified material. In the obtained dried powder (E$_1$), the content rate of particles of 25 μm or less was 0.2% by mass, and the mean particle diameter was 54 μm. The content rate of particles and the mean particle diameter were measured by LS230 (trade name) manufactured by BECKMAN COULTER (the same will apply hereafter).
(Calcination of Dried Powder (E$_1$))

The obtained dried powder (E$_1$) was supplied in the supplied amount of 80 g/hr to a continuous SUS cylindrical calcining tube which has a rotary furnace diameter (inner diameter; the same will apply hereafter) of 3 inches and a length of 89 cm. A nitrogen gas of 1.5 NL/min was flowed in a direction opposed to the supply direction of the dried powder (that is, countercurrent flow; the same will apply hereafter) and the same direction (that is, concurrent flow; the same will apply hereafter) respectively in the calcining tube, and the total flow rate was set to 3.0 NL/min. The temperature of the furnace was set such that the temperature of the calcining tube was raised over 4 hours to 360° C. as the maximum calcining temperature while the calcining tube was rotated at a speed of 4 rotation/min, and the temperature could be held at 360° C. for 1 hour, to perform preliminary calcination. A small amount of the preliminary calcined body collected at the outlet of the calcining tube was sampled, and heated to 400° C. in a nitrogen atmosphere. The reduction rate was then measured. The reduction rate was 10.2%. The collected preliminary calcined body was supplied in the supplied amount of 60 g/hr to a continuous SUS cylindrical calcining tube which has a rotary furnace diameter of 3 inches and a length of 89 cm. A nitrogen gas of 1.1 NL/min was flowed in a direction opposed to the supply direction of the dried powder and the same direction respectively in the calcining tube, and the total flow rate was set to 2.2 NL/min. The temperature of the furnace was set such that the temperature could be raised to 680° C. over 2 hours, held at 680° C. for 2 hours, and then lowered to 600° C. over 8 hours, to perform final calcination.
(Removal of Projection Substance)

50 g of a calcined body (F$_1$) was put in a perpendicular tube (inner diameter: 41.6 mm, length: 70 cm) wherein a perforated disk having three holes each having a diameter of ¹⁄₆₄ inches was provided in a bottom part and a paper filter was provided in an upper part. Then, air was circulated at room temperature towards the upper part from the lower part of the perpendicular tube via each hole, to urge the contact of the calcined bodies. An air current length in the direction in which the air current at this time flowed was 56 mm, and the mean linear speed of the air current was 332 m/s. The projection substance was not present in the composite oxide catalyst (G$_1$) obtained after 24 hours.

An a/b composition ratio of the composite oxide catalyst (G$_1$) was measured by X-ray fluorescence analysis (apparatus: manufactured by Rigaku Corporation, RINT1000 (trade name), Cr tube, tube voltage: 50 kV, tube current: 50 mA, and the same will apply hereafter). The obtained results are shown in Table 1. The composition of the composite oxide catalyst (G$_1$) obtained at this time was Mo$_1$V$_{0.190}$Sb$_{0.200}$Nb$_{0.102}$W$_{0.03}$Ce$_{0.005}$O$_n$/53.2 wt %-SiO$_2$.
(Ammoxidation Reaction of Propane)

Propane was provided for a vapor-phase catalytic ammoxidation reaction by the following method using the composite oxide catalyst (G$_1$) obtained above. A Vycor glass fluidized-bed reaction tube having an inner diameter of 25 mm was filled with 35 g of the composite oxide catalyst. A mixed gas having a molar ratio of propane:ammonia:oxygen:helium of 1:1:3:18 was supplied into the reaction tube at a contact time of 3.0 (sec·g/cm$^3$) at a reaction temperature of 440° C. under an atmospheric pressure as a reaction pressure. The reaction yields of acrylonitrile (AN) when a successive reaction is performed for 30 days for the catalyst are shown in Table 1.

Examples 2 to 9 and Comparative Examples 1 to 8

Catalysts having compositions shown in Table 1 were prepared, and the ammoxidation reaction of propane was performed by the same method as that in Example 1 using the catalysts. The yields of the reactions using the catalysts are shown in Table 1.

TABLE 1

| | Mo/V | a(V)/b(Sb) | V | Sb | Nb | W | Z | SiO$_2$ (wt %) | AN yield (%) | CO$_2$ + CO yield (%) |
|---|---|---|---|---|---|---|---|---|---|---|
| | | | | | | | Compositions after removing projection body (Based on Mo = 1.0) | | | |
| Example 1 | 5.3 | 0.95 | 0.190 | 0.200 | 0.100 | 0.03 | Ce 0.005 | 53.2 | 54.9 | 24.5 |
| Example 2 | 5.3 | 0.63 | 0.188 | 0.300 | 0.099 | 0.03 | Ce 0.005 | 54.4 | 54.0 | 25.4 |
| Example 3 | 6.9 | 0.94 | 0.145 | 0.155 | 0.102 | 0.03 | Ce 0.005 | 55.2 | 54.7 | 24.7 |
| Example 4 | 5.3 | 0.85 | 0.188 | 0.220 | 0.103 | 0.03 | Ce 0.005 | 52.6 | 54.9 | 24.5 |
| Example 5 | 6.7 | 0.68 | 0.150 | 0.219 | 0.095 | 0.03 | Ce 0.005 | 53.3 | 54.6 | 24.8 |
| Example 6 | 5.1 | 0.84 | 0.195 | 0.233 | 0.109 | 0.03 | Ce 0.006 | 52.3 | 55.2 | 24.2 |
| Example 7 | 6.7 | 0.79 | 0.150 | 0.190 | 0.102 | 0.03 | Ce 0.006 | 51.9 | 55.0 | 24.4 |
| Example 8 | 8.3 | 0.65 | 0.120 | 0.185 | 0.105 | 0.03 | Ce 0.006 | 52.0 | 53.6 | 25.8 |
| Example 9 | 8.5 | 0.84 | 0.118 | 0.140 | 0.103 | 0.03 | Ce 0.006 | 49.3 | 53.5 | 25.9 |
| Comparative Example 1 | 5.9 | 1.06 | 0.170 | 0.160 | 0.100 | 0.03 | Ce 0.005 | 52.7 | 51.5 | 28.3 |
| Comparative Example 2 | 6.7 | 0.56 | 0.150 | 0.270 | 0.090 | 0.03 | Ce 0.005 | 55.0 | 51.8 | 28.0 |
| Comparative Example 3 | 4.3 | 0.88 | 0.230 | 0.260 | 0.092 | 0.03 | Ce 0.005 | 51.0 | 52.3 | 28.9 |
| Comparative Example 4 | 11.1 | 0.90 | 0.090 | 0.100 | 0.090 | 0.03 | Ce 0.006 | 52.0 | 48.1 | 32.1 |
| Comparative Example 5 | 6.7 | 1.03 | 0.150 | 0.145 | 0.090 | 0.03 | Ce 0.005 | 49.6 | 52.4 | 27.4 |
| Comparative Example 6 | 6.7 | 0.58 | 0.150 | 0.260 | 0.102 | 0.03 | Ce 0.005 | 52.1 | 52.0 | 27.8 |
| Comparative Example 7 | 5.0 | 0.65 | 0.200 | 0.310 | 0.105 | 0.03 | Ce 0.007 | 53.0 | 53.0 | 27.1 |
| Comparative Example 8 | 11.1 | 0.78 | 0.090 | 0.115 | 0.090 | 0.03 | Ce 0.008 | 54.0 | 50.0 | 30.9 |

From the results of Examples, it was shown that the catalysts of the present embodiment have a high AN yield, and a low CO$_2$ and CO yield. Particularly, the CO$_2$ and CO yields are remarkably decreased as compared with Comparative Examples, therefore it can be presumed that and the decomposition of not only acrylonitrile but a useful by-product such as acetonitrile or hydrocyanic acid is also suppressed.

The present application is based on Japanese Patent Application (Japanese Patent Application No. 2012-214867) filed to the Japan Patent Office on Sep. 27, 2012, and the contents thereof are incorporated herein by reference.

INDUSTRIAL APPLICABILITY

The composite oxide catalyst of the present invention can be suitably used as a catalyst which can suppress the generation of CO$_2$ and CO, and improve the yield of an unsaturated nitrile in a method for subjecting propane or isobutane to a vapor-phase catalytic ammoxidation reaction to produce a corresponding unsaturated nitrile.

The invention claimed is:

1. A composite oxide catalyst used for a vapor-phase catalytic oxidation reaction or vapor-phase catalytic ammoxidation reaction of propane or isobutane, the composite oxide catalyst comprising a composite oxide represented by the following composition formula (1):

$$Mo_1V_aSb_bNb_cW_dZ_eO_n \quad (1),$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 0.85$.

2. The composite oxide catalyst according to claim 1, further comprising 20 to 70% by mass of silica in terms of SiO$_2$.

3. A method for producing a composite oxide catalyst comprising a composite oxide represented by the following composition formula (1):

$$Mo_1V_aSb_bNb_cW_dZ_eO_n \quad (1)$$

wherein the component Z is one or more element selected from the group consisting of La, Ce, Pr, Yb, Y, Sc, Sr, and Ba; a, b, c, d, e, and n represent atomic ratios of the elements; and $0.1 \leq a < 0.2$, $0.15 \leq b \leq 0.5$, $0.01 \leq c \leq 0.5$, $0 \leq d \leq 0.4$, $0 \leq e \leq 0.2$ and $0.60 < a/b < 0.85$, the method comprising:
(I) a raw material blending step of preparing a raw material blending liquid which comprises Mo, V, Sb, Nb, W, and Z and in which $0.1 \leq a < 0.2$, $0.15 \leq b \leq 0.5$, $0.01 \leq c \leq 0.5$, $0 \leq d \leq 0.4$, $0 \leq e \leq 0.2$, and $0.60 < a/b < 0.85$ for the atomic ratios;
(II) a drying step of drying the raw material blending liquid to obtain a dried powder;
(III) a calcining step of calcining the dried powder to obtain a calcined body; and
(IV) a projection substance removing step of removing a projection substance present on a particle surface of the calcined body.

4. The method for producing the composite oxide catalyst according to claim 3, wherein the raw material blending step (I) comprising the steps of:
(a) preparing an aqueous mixed liquid containing Mo, V, Sb, and the component Z;
(b) adding silica sol and hydrogen peroxide water to the aqueous mixed liquid obtained in the (a) step;
(c) mixing the solution obtained in the (b) step with an aqueous solution containing Nb, dicarboxylic acid, and hydrogen peroxide water, and a W-containing compound; and
(d) adding a powder silica-containing suspension liquid to the solution obtained in the (c) step to age the solution.

5. A method for producing a corresponding unsaturated nitrile by subjecting propane or isobutane to a vapor-phase catalytic oxidation reaction or a vapor-phase catalytic ammoxidation reaction, the corresponding unsaturated nitrile being derived from the propane and isobutene, wherein the composite oxide catalyst according to claim 1 is used.

6. A method for producing a corresponding unsaturated nitrile by subjecting propane or isobutane to a vapor-phase catalytic oxidation reaction or a vapor-phase catalytic ammoxidation reaction, the corresponding unsaturated nitrile being derived from the propane and isobutene, wherein the composite oxide catalyst according to claim 2 is used.

7. The composite oxide catalyst according to claim 1, wherein $0.60 < a/b < 0.79$.

8. The composite oxide catalyst according to claim 1, wherein the component Z is Ce.

\* \* \* \* \*